(12) United States Patent
Lachenbruch et al.

(10) Patent No.: US 9,463,124 B2
(45) Date of Patent: Oct. 11, 2016

(54) MICROCLIMATE SYSTEM FOR A PATIENT SUPPORT APPARATUS

(71) Applicant: Hill-Rom Services, Inc., Batesville, IN (US)

(72) Inventors: Charles A. Lachenbruch, Lakeway, TX (US); Rachel L. Williamson, Batesville, IN (US); Katherine M. McDonnell, Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 14/156,085

(22) Filed: Jan. 15, 2014

(65) Prior Publication Data

US 2014/0196210 A1 Jul. 17, 2014

Related U.S. Application Data

(60) Provisional application No. 61/752,837, filed on Jan. 15, 2013.

(51) Int. Cl.
*A47C 21/04* (2006.01)
*A61G 7/00* (2006.01)
(Continued)

(52) U.S. Cl.
CPC .............. *A61G 7/001* (2013.01); *A61F 7/0053* (2013.01); *A61G 7/018* (2013.01); *A61G 7/05769* (2013.01); *A61F 7/007* (2013.01); *A61F 7/0085* (2013.01); *A61F 7/0097* (2013.01); *A61F 2007/006* (2013.01); *A61F 2007/0096* (2013.01); *A61F 2007/0258* (2013.01); *A61G 7/015* (2013.01); *A61G 2007/05784* (2013.01); *A61G 2203/12* (2013.01); *A61G 2203/16* (2013.01); *A61G 2203/20* (2013.01);
(Continued)

(58) Field of Classification Search
CPC ........................................................ A47C 21/04
USPC .................. 5/421, 423, 713–715, 724, 652.1
See application file for complete search history.

(56) References Cited

U.S. PATENT DOCUMENTS 2,726,294 A 12/1955 Kroening et al.
2,924,832 A 2/1960 Knowles
(Continued)

FOREIGN PATENT DOCUMENTS

EP 0862901 9/1998
EP 1779824 5/2007
(Continued)

OTHER PUBLICATIONS

European Search Report, "Application No. EP 10251104," (Sep. 27, 2010), The Hague.
(Continued)

*Primary Examiner* — Frederick Conley
(74) *Attorney, Agent, or Firm* — Barnes & Thornburg LLP

(57) ABSTRACT

According to the present disclosure, a microclimate system includes a topper and an air box. The topper is configured to conduct air along a surface of the topper so that heat and moisture from a patient lying on the topper are drawn away from the surface. The air box includes a blower coupled to the topper to provide air to the topper to be conducted along the surface of the topper. The air box may also include an environmental sensor unit coupled configured to detect environmental information corresponding to the environment around the microclimate system.

21 Claims, 9 Drawing Sheets

(51) Int. Cl.
*A61G 7/018* (2006.01)
*A61G 7/057* (2006.01)
*A61F 7/00* (2006.01)
A61G 7/015 (2006.01)
A61F 7/02 (2006.01)

(52) U.S. Cl.
CPC ...... *A61G 2203/34* (2013.01); *A61G 2203/46* (2013.01); *A61G 2210/70* (2013.01); *A61G 2210/90* (2013.01)

(56) References Cited

U.S. PATENT DOCUMENTS

| | | | |
|---|---|---|---|
| 3,245,068 A | 4/1966 | Wegryn et al. |
| 3,678,928 A | 7/1972 | Mozes |
| 3,738,702 A | 6/1973 | Jacobs |
| 3,757,356 A | 9/1973 | Freeman |
| 3,888,259 A | 6/1975 | Miley |
| 4,620,333 A | 11/1986 | Ritter |
| 4,870,710 A | 10/1989 | Hartmann |
| 4,970,736 A | 11/1990 | Koizumi |
| 5,081,722 A | 1/1992 | Yu |
| 5,144,284 A | 9/1992 | Hammett |
| 5,291,181 A | 3/1994 | DePonte |
| 5,380,278 A | 1/1995 | Mombrinie |
| 5,438,721 A | 8/1995 | Pahno et al. |
| 5,459,452 A | 10/1995 | DePonte |
| 5,588,167 A | 12/1996 | Pahno et al. |
| 5,640,728 A | 6/1997 | Graebe |
| 5,800,480 A | 9/1998 | Augustine et al. |
| 5,827,246 A | 10/1998 | Bowen |
| 6,011,477 A | 1/2000 | Teodorescu et al. |
| 6,033,432 A | 3/2000 | Augustine et al. |
| 6,202,689 B1 | 3/2001 | Williams |
| 6,384,728 B1 | 5/2002 | Kanor et al. |
| 6,450,995 B1 | 9/2002 | Prabhakar |
| 6,583,722 B2 | 6/2003 | Jeutter et al. |
| 6,772,825 B2 | 8/2004 | Lachenbruch et al. |
| 6,892,734 B1 | 5/2005 | Schleicher et al. |
| 7,273,490 B2 | 9/2007 | Lachenbruch |
| 7,727,267 B2 | 6/2010 | Lachenbruch |
| 7,914,611 B2 | 3/2011 | Vrzalik et al. |
| 7,939,706 B2 | 5/2011 | Okabe et al. |
| 7,962,981 B2 | 6/2011 | Lemire et al. |
| 8,281,434 B2 | 10/2012 | Skripps |
| 8,327,477 B2 | 12/2012 | Lachenbruch et al. |
| 8,578,527 B2 | 11/2013 | Lachenbruch et al. |
| 2004/0216235 A1 | 11/2004 | Rees |
| 2004/0236292 A1 | 11/2004 | Tazoe et al. |
| 2005/0288749 A1 | 12/2005 | Lachenbruch |
| 2006/0015080 A1 | 1/2006 | Mahnensmith |
| 2006/0085919 A1 | 4/2006 | Kramer et al. |
| 2006/0162074 A1 | 7/2006 | Bader |
| 2006/0168736 A1 | 8/2006 | Meyer et al. |
| 2007/0135878 A1 | 6/2007 | Lachenbruch et al. |
| 2007/0261548 A1 | 11/2007 | Vrzalik et al. |
| 2007/0266499 A1 | 11/2007 | O'Keefe et al. |
| 2007/0272673 A1 | 11/2007 | Keane |
| 2008/0263763 A1* | 10/2008 | Butler ..................... 5/81.1 R |
| 2010/0005588 A1 | 1/2010 | Christopher |
| 2010/0016818 A1 | 1/2010 | Mahnensmith |
| 2010/0043143 A1 | 2/2010 | O'Reagan et al. |
| 2010/0175196 A1 | 7/2010 | Lafleche et al. |
| 2010/0325796 A1 | 12/2010 | Lachenbruch et al. |
| 2011/0010014 A1* | 1/2011 | Oexman et al. ............. 700/276 |
| 2011/0115635 A1 | 5/2011 | Petrovski et al. |
| 2011/0219548 A1 | 9/2011 | Vrzalik et al. |
| 2011/0258778 A1* | 10/2011 | Brykalski et al. ................ 5/421 |
| 2012/0012277 A1* | 1/2012 | Lachenbruch ....... A47C 21/044 165/60 |
| 2013/0019405 A1 | 1/2013 | Flanagan et al. |
| 2013/0167296 A1 | 7/2013 | Smith |
| 2013/0298330 A1 | 11/2013 | Lachenbruch et al. |
| 2014/0041118 A1 | 2/2014 | Lachenbruch et al. |
| 2014/0059766 A1 | 3/2014 | Gibson et al. |

FOREIGN PATENT DOCUMENTS

| | | |
|---|---|---|
| WO | 2006/023479 | 3/2006 |
| WO | 2007/016054 | 2/2007 |

OTHER PUBLICATIONS

Paul A. Iaizzo, PhD, Craig L. Kveen, BS, Jaydeep Y. Kokate, MS, Keith J. Leland, BS, Gary L. Hansen, MS, Ephraim M. Sparrow, PhD, Prevention of Pressure Ulcers by Focal Cooling: Histological Assessment in a Porcine Model, Wounds 1995: 7(5): 161-169, Sep./Oct. 1995.

Extended European Search Report for Application No. EP 13 19 0107.6 dated Nov. 13, 2013, 7 pages.

* cited by examiner

MICROCLIMATE SYSTEM FOR A PATIENT SUPPORT APPARATUS

CROSS-REFERENCE TO RELATED APPLICATIONS

The present application claims the benefit, under 35 U.S.C. §119(e), of U.S. Provisional Application No. 61/752,837, which was filed Jan. 15, 2013, and which is hereby incorporated by reference herein in its entirety.

BACKGROUND

The present disclosure is related to microclimate systems, and in particular to microclimate control systems used in patient supports, such as hospital beds. The present disclosure may also be applicable to other types of patient supports, such as recovery beds, wheel chairs, surgical tables and the like.

Microclimate systems are typically used to cool and dry a patient's skin around the interface of the patient's skin with a support surface. Cool and dry skin is helpful to patient health and is less likely to develop decubitus ulcers (bed sores) during stays on a patient support.

Some microclimate systems blow air along the interface of a patient's skin with a support surface. Such systems may be rated to remove a predetermined amount of heat and moisture from a patient's skin when operated. Sometimes, microclimate systems that are rated to remove predetermined amounts of heat and moisture can fail to perform at rated levels due to environmental conditions, for example high temperatures and/or high humidity in the environment surrounding the microclimate system.

SUMMARY

The present application discloses one or more of the features recited in the appended claims and/or the following features which, alone or in any combination, may comprise patentable subject matter:

According to the present disclosure, a microclimate system may include a support surface and an air box. The support surface may include a topper. The topper may be configured to conduct air along a top face of the support surface so that heat and moisture from a patient lying on the support surface are drawn away from the top face of the support surface. The air box may include a controller and a blower. The blower may be coupled to the controller for electrical communication and may be coupled to the topper.

In illustrative embodiments, the air box may include an environmental sensor unit coupled the controller. The environmental sensor unit may be configured to detect environmental information.

In illustrative embodiments, the controller may be configured to receive the environmental information from the environmental sensor unit. The controller may also determine if current operating parameters of the air box provide a rated level of heat withdrawal and/or evaporative capacity through the topper based at least in part on the environmental information. The controller may then update the current operating parameters of the air box if the current operating parameters of the air box do not provide the rated level of heat withdrawal and/or evaporative capacity through the topper.

In illustrative embodiments, the environmental sensor unit may include a temperature sensor, a humidity sensor, or a pressure sensor. It is contemplated that the environmental sensor unit may include a temperature sensor and a humidity sensor.

In illustrative embodiments, the controller may determine if current operating parameters of the air box will provide the rated level of heat withdrawal and/or evaporative capacity through the topper based at least in part on the environmental information by (i) looking up an actual level of heat withdrawal and evaporative capacity corresponding to the detected environmental information in a first look-up table and (ii) comparing the actual level of heat withdrawal and/or evaporative capacity parameters with the rated level of heat withdrawal and evaporative capacity. The controller may update the current operating parameters of the air box by (i) looking up new operating parameters corresponding to the detected environmental information in a second look-up table and (ii) changing the current operating parameters to the new operating parameters.

In illustrative embodiments, the air box may include a conditioning unit coupled to the controller for electrical communication with the controller. The conditioning unit may be coupled between the blower and the topper for pneumatic communication with both the blower and the topper.

In illustrative embodiments, the conditioning unit may include a heater configured to warm air moving from the blower to the topper and/or a cooler configured to cool air moving from the blower to the topper. The operating parameters of the air box may include blower speed settings and conditioning unit power settings.

In illustrative embodiments, the support surface may include inflatable body bladders encased by a lower ticking and the topper. The inflatable body bladders may be coupled to the blower for pneumatic communication. The inflatable body bladders may be configured to support a patient lying on the support surface.

In illustrative embodiments, the support surface may include a left turn bladder and a right turn bladder encased by the lower ticking and the topper. The left and the right turn bladder may be coupled to the blower for pneumatic communication. The left and the right turn bladder may be configured to rotate a patient lying on the support surface about a longitudinal axis of the support surface.

According to the present disclosure, a microclimate system may include a topper, and an air box. The air box may include a controller and a blower. The blower may be coupled to the controller for electrical communication with the controller and may be coupled to the topper for pneumatic communication with the topper.

In illustrative embodiments, the air box may include an environmental sensor unit coupled the controller for electrical communication with the controller. The environmental sensor unit may be configured to detect environmental information.

In illustrative embodiments, the controller may be configured to receive the environmental information from the environmental sensor unit. The controller may also be configured to determine if current operating parameters of the air box provide a rated level of heat withdrawal and/or evaporative capacity through the topper based at least in part on the environmental information. The controller may then update the current operating parameters of the air box if the current operating parameters of the air box do not provide the rated level of heat withdrawal and/or evaporative capacity through the topper.

In illustrative embodiments, the air box may include a housing encasing the blower and a connector hose extending from the housing to the topper. In some embodiments, the environmental sensor unit may be encased in the housing.

In illustrative embodiments, the air box includes a conditioning unit coupled to the controller for electrical communication and coupled between the blower and the topper for pneumatic communication. The conditioning unit may include a heater configured to warm air moving from the blower to the topper and/or a cooler configured to cool air moving from the blower to the topper. In some embodiments, the operating parameters of the air box may include blower speed settings and conditioning unit power settings.

According to the present disclosure, a method for controlling a microclimate system is taught. The microclimate system may include a topper and an air box coupled to the topper to provide pressurized air to the topper. The method may include the steps of receiving information from a sensor unit corresponding to air temperature and air humidity, determining if current operating parameters of the air box provide a rated level of heat withdrawal and/or evaporative capacity through the topper based at least in part on the information, and updating the current operating parameters of the air box if the current operating parameters of the air box do not provide the rated level of heat withdrawal and/or evaporative capacity through the topper.

In illustrative embodiments, the step of determining if current operating parameters of the air box will provide the rated level of heat withdrawal and evaporative capacity may include (i) looking up an actual level of heat withdrawal and/or evaporative capacity corresponding to the received information in a first look-up table and (ii) comparing the actual level of heat withdrawal and/or evaporative capacity parameters with the rated level of heat withdrawal and/or evaporative capacity. The step updating the current operating parameters of the air box may include (i) looking up new operating parameters corresponding to the received information in a second look-up table and (ii) changing the current operating parameters to the new operating parameters.

In illustrative embodiments, the step of determining if current operating parameters of the air box will provide the rated level of heat withdrawal or evaporative capacity may include (i) calculating an actual level of heat withdrawal or evaporative capacity corresponding to the received information using a first equation and (ii) comparing the actual level of heat withdrawal or evaporative capacity with the rated level of heat withdrawal and evaporative capacity.

In illustrative embodiments, the information received may correspond to environmental temperature, environmental humidity, or environmental pressure.

Additional features alone or in combination with any other feature(s), including those listed above and those listed in the claims and those described in detail below, can comprise patentable subject matter. Others will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
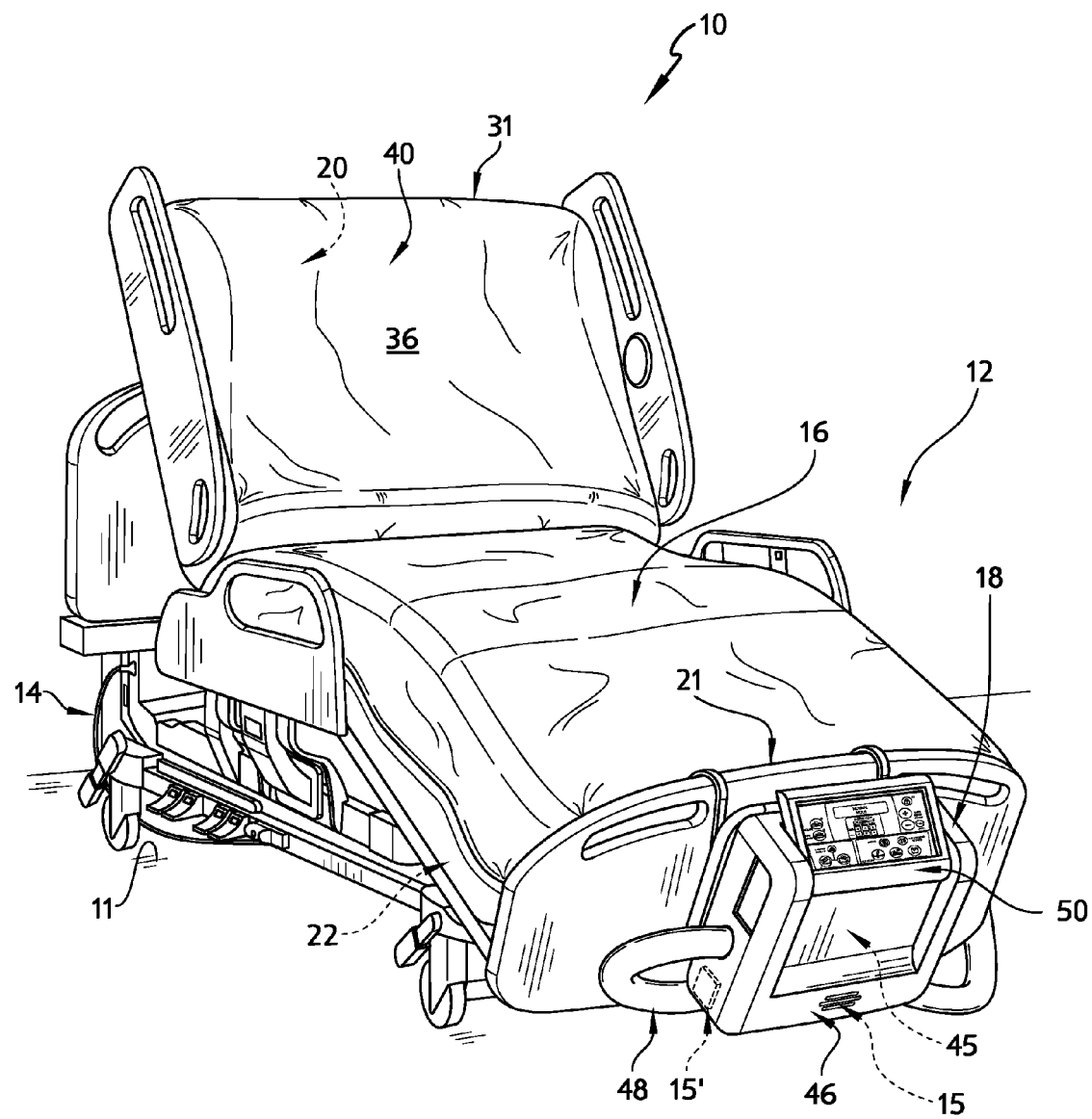
FIG. 1 is perspective view of an illustrative patient support apparatus including a microclimate system supported on a frame structure showing that the microclimate system includes a support surface and an air box coupled to the support surface.

An illustrative patient support apparatus embodied as a hospital bed 10 is shown in FIG. 1. The bed 10 includes a microclimate system 12 mounted on a frame structure 14 that supports the microclimate system 12 above a floor 11. The microclimate system 12 is arranged to underlie a patient supported on the bed 10. The microclimate system 12 is configured to cool and dry the interface between a patient and the bed 10 to promote skin health by moving air along the interface when the patient is supported on the bed 10. The microclimate system 12 illustratively includes an environmental sensor unit 15 configured to detect information about the environment around the microclimate system 12 so that operation of the microclimate system 12 can be adjusted to account for environmental temperature, humidity, and/or pressure.

Figure 2:
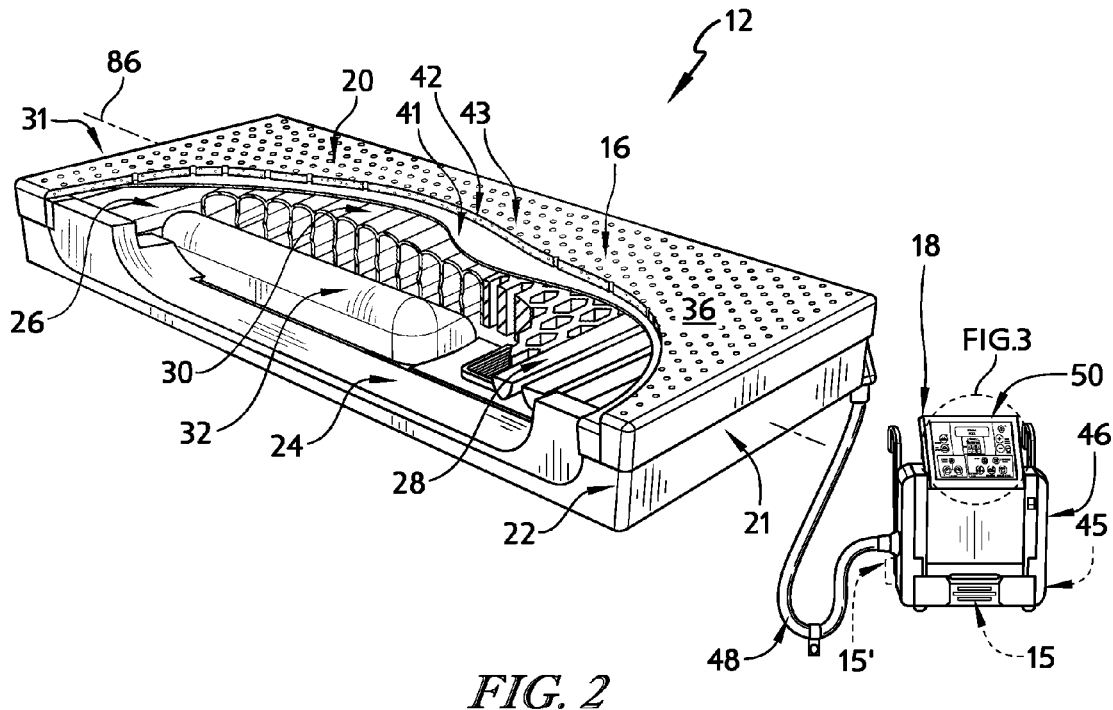
FIG. 2 is a perspective view of the microclimate system of FIG. 1 showing that the support surface includes a topper that cooperates with a lower ticking to enclose the other components of the support surface, and showing that the air box is coupled to the topper via a connector hose to provide air to the topper.

Referring now to FIG. 2, the illustrative microclimate system 12 illustratively includes a support surface 16, an air box 18, and the environmental sensor unit 15. The support surface 16 (sometimes called a mattress) is configured to underlie a patient supported on the bed 10. The air box 18 is coupled to the support surface 16 and is configured to provide conditioned air to the support surface 16 in order to cool and dry the interface between a patient and the support surface 16 when the patient is supported on the bed 10.

The support surface 16 includes a topper 20 and a lower ticking 22 that cooperate to encase a foam shell 24, a foam head section 26, a foam foot section 28, body bladders 30, and turn bladders 32 as shown, for example, in FIG. 2. The topper 20 forms a top face 36 of the support surface 16 and is configured to conduct conditioned air provided by the air box 18 along the interface between a patient and the support surface 16 when the patient is supported on the bed 10. The foam components 24, 26, 28 and the bladders 30, 32 cooperate to support a patient when the patient is supported on the bed 10. In some embodiments, the support surface 16 may also include a coverlet 40 encasing the topper 20 and the lower ticking 22 as shown in FIG. 1.

The topper 20 illustratively includes a bottom layer 41, a middle layer 42, and a top layer 43 as shown in FIG. 2. The middle layer 42 is illustratively a three-dimensional material that allows conditioned air to flow between the bottom layer 41 and the top layer 43 along the top face 36 of the support surface 16 from a foot end 21 to a head end 31 of the support surface 16 as suggested by arrows 44 in FIG. 4. The top layer 43 is made from a perforated material that allows moisture from a patient supported on the topper 20 to pass through the top layer 43 and be carried away for evaporation by conditioned air flowing through the middle layer 42 of the topper 20.

In other embodiments, other air-flow cooled toppers may be used with the support surface 16. For example, air-loss toppers, air-fluidized bead toppers, and the like can be used in support surface 16.

The air box 18 is illustratively is adapted to be mounted on the frame structure 14, as shown in FIG. 1, but in other embodiments may be integrated into the frame structure 14. The air box 18 is coupled to the support surface 16 to provide air to the support surface 16, as shown in FIG. 2.

Figure 3:
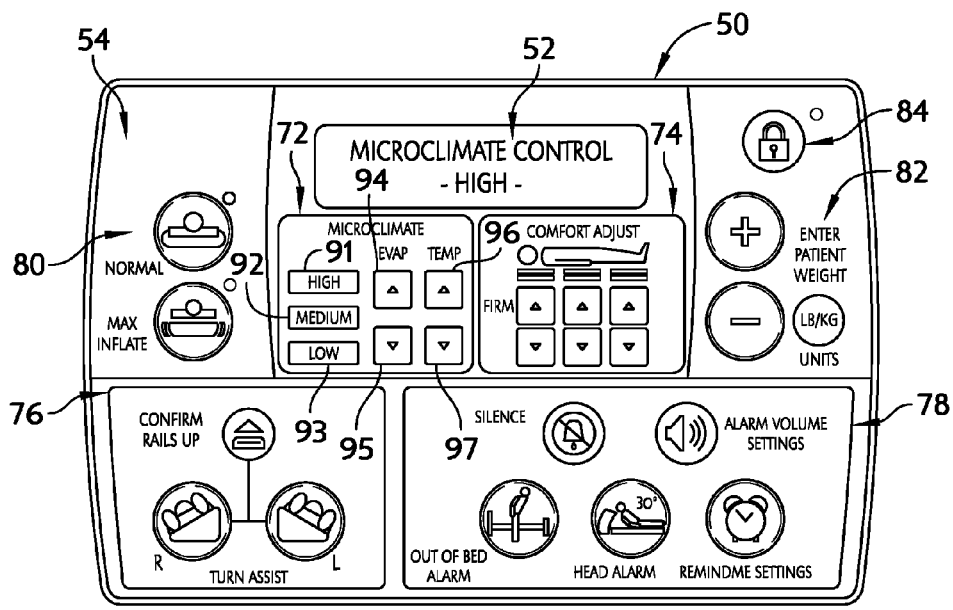
FIG. 3 is a detail view of an illustrative user interface included in the air box of FIGS. 1 and 2 showing that the user interface includes buttons configured to control air box settings.

The air box 18 includes the environmental sensor unit 15, a air handling unit 45, a housing 46, a connector hose 48, and a user interface 50 as shown in FIG. 2. The housing 46 holds the environmental sensor unit 15 and the air handling unit 45 as suggested in FIGS. 1 and 2. The connector hose 48 extends from the housing 46 to the support surface 16 to couple the air handling unit 45 to the support surface 16. The user interface 50 is coupled to the housing 46 and includes an LCD display 52 and a number of push buttons 54 as shown in FIG. 3. In other embodiments, the user interface 50 may be a touch screen or another suitable interface.

Figure 4:
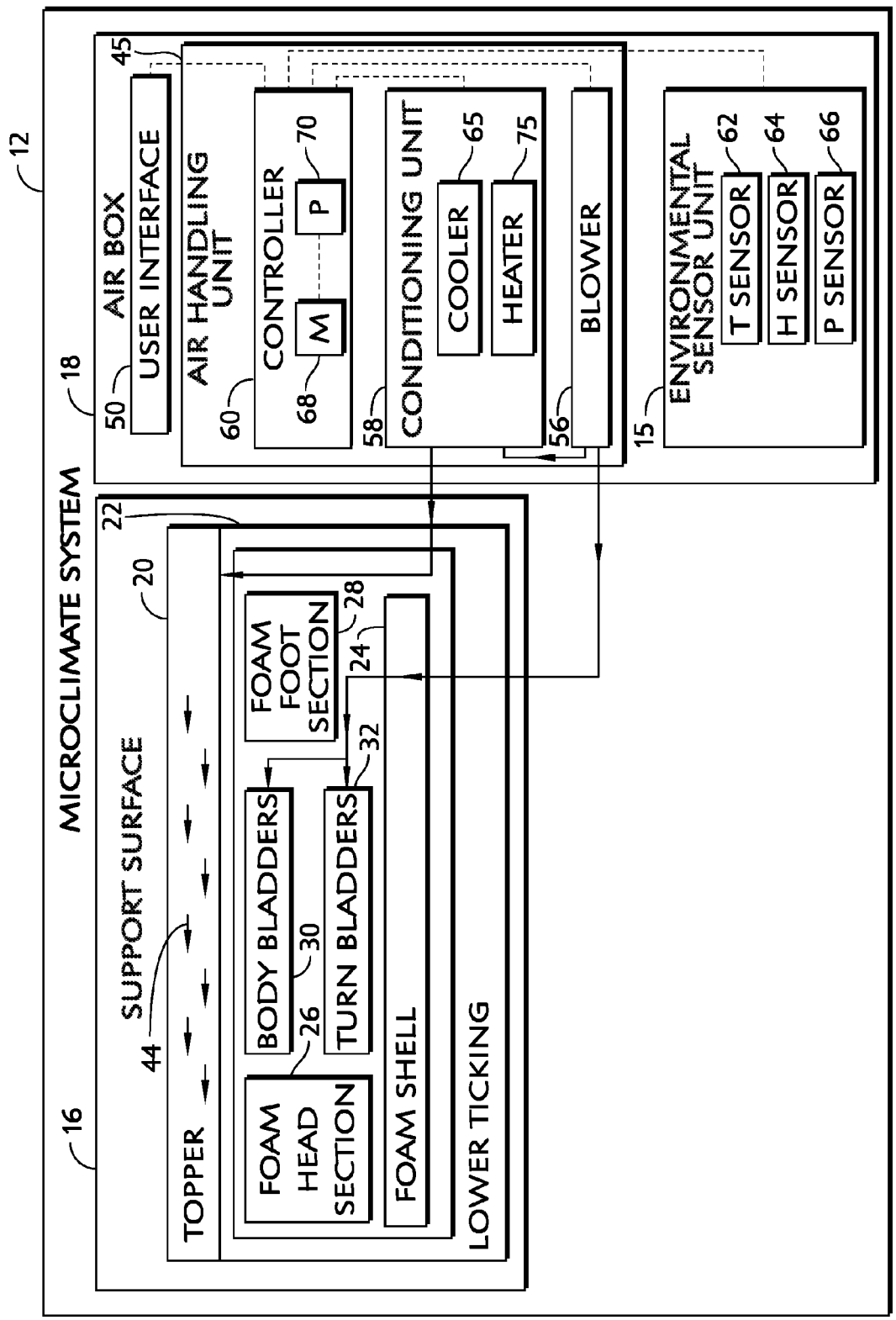
FIG. 4 is a diagrammatic view of the microclimate system of FIGS. 1 and 2 showing that the air box includes an air handling unit with a controller, a blower, and an air conditioner unit, and showing that the air box includes an environmental sensor unit coupled to the controller to provide the controller with information about environmental conditions.

Referring now to FIG. 4, the air handling unit 45 is shown to include a blower 56, a conditioning unit 58, and a controller 60. The blower 56 is coupled to the topper 20 (through the conditioning unit 58) and the bladders 30, 32 to provide air flow to the topper 20 and the bladders 30, 32. The conditioning unit 58 is coupled between the blower 56 and the topper 20 and is configured to condition air moved from the blower 56 to the topper 20. The controller 60 is illustratively coupled to the user interface 50 to send and receive information to/from a user. The blower 56 and the conditioning unit 58 are also electrically coupled to the controller 60 as shown in FIG. 4. Pneumatic connections are illustrated in FIG. 4 using solid lines with arrows suggesting the direction of flow and electrical connections are illustrated in FIG. 4 with dotted lines.

The conditioning unit 58 includes a cooler 65 and a heater 75 that are configured to cool or heat air sent from the blower 56 to the topper 20 as show in FIG. 4. In some embodiments, the conditioning unit 58 may also include a humidifier (not shown) and/or a dehumidifier (not shown) configured to add or remove humidity from air passed from the blower 56 to the topper 20. In some embodiments, the conditioning unit may be omitted or may include other combinations of a cooler, a heater, a humidifier, and/or a dehumidifier.

Figure 4A:
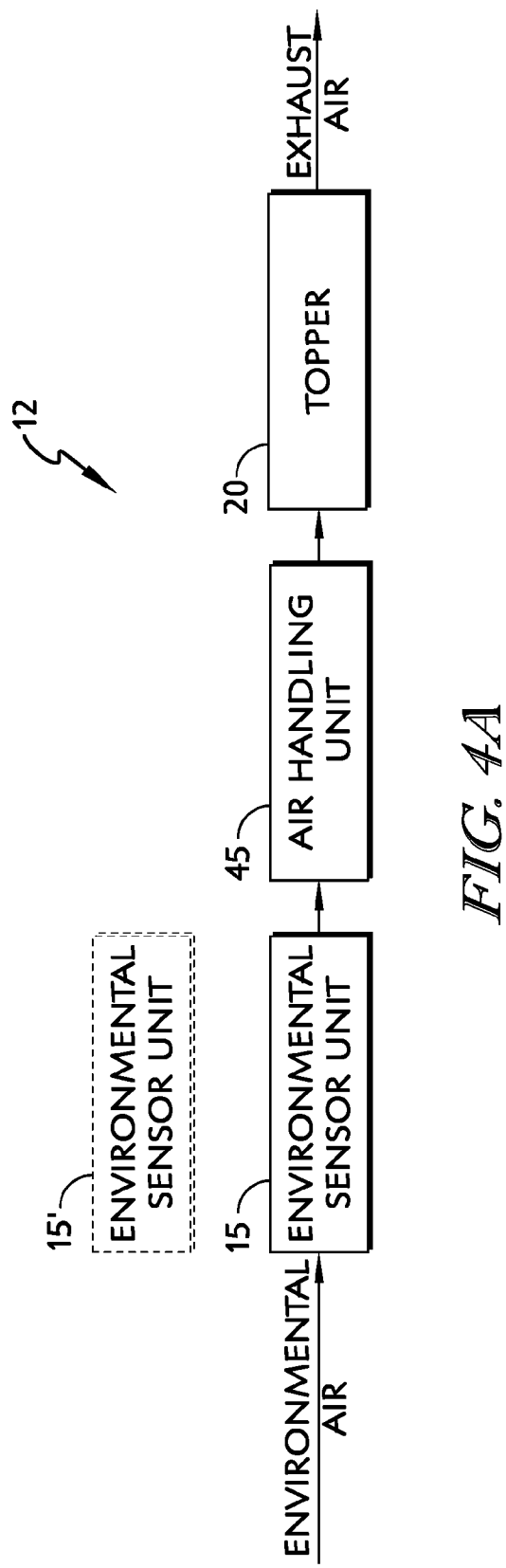
FIG. 4A is a diagrammatic pneumatic flow diagram showing the that environmental air is passed over the environmental sensor unit before entering the air handling unit and being sent to the topper.

The environmental sensor unit 15 is illustratively housed in the housing 46 of the air box along an intake path of the blower 56. In other embodiments, the environmental sensor unit 15 may be located outside the housing 46 and/or spaced apart from the intake path of the blower 56 as suggested by alternative environmental sensor unit 15' shown in FIGS. 1, 2, and 4A.

The environmental sensor unit 15 of the illustrative embodiment, includes a temperature sensor 62, a humidity sensor 64, and a pressure sensor 66 as shown, diagrammatically, in FIG. 4. Each of the sensors 62, 64, 66 included in the environmental sensor unit 15 is configured to detect an environmental factor corresponding to the surroundings of the support surface 16 and the air box 18. Each of the sensors 62, 64, 66 is also coupled to the controller 60 to communicate the detected environmental factors to the controller 60.

As shown in FIG. 4, the controller 60 illustratively includes a memory 68 configured store information and instructions and a processor 70 coupled to the memory 68 to execute the instructions held in the memory 68. The controller 60 is configured to adjust operation of the air box 18 based on the environmental factors provided by the sensors 62, 64, 66. More specifically, the controller 60 is configured to adjust the operation of the air box 18 to provide a rated level of heat and moisture withdrawal through the top face 36 of the support surface 16 by adjusting the flow and temperature of conditioned air from the air box 18 to the support surface 16 based on the environmental factors provided by the sensors 62, 64, 66. In other embodiments, the environmental sensor unit 15 may only include one or two of the sensors 62, 64, 66 or may include other types of sensors configured to detect environmental factors corresponding to the surroundings of the support surface 16 and the air box 18.

Referring now to FIG. 3, the user interface 50 includes push buttons 54 adapted to provide user inputs to the controller 60. The push buttons 54 are organized to provide a microclimate control panel 72, a comfort control panel 74, a turn-assist control panel 76, an alarm panel 78, an inflation control panel 80, a weight entry panel 82, and a user interface lock button 84 as shown in FIG. 3. Each panel 72, 74, 76, 78, 80 is configured to control a different aspect of the microclimate system 12.

The microclimate control panel 72 is configured to allow a user to automatically or manually control the microclimate system 12 as suggested in FIG. 3. Specifically, a user may select an automatic (or predetermined) level of microclimate control desired from the microclimate system 12 by pressing a high, medium, or low button 91, 92, 93. Alternatively, a user may select custom levels of moisture removal and interface temperature by pressing up and down arrows 94, 95, 96, and 97.

In the illustrative embodiment, each of the automatic levels of microclimate control and each custom level of microclimate control is associated with corresponding preset levels of microclimate system 12 performance. Automatic levels of microclimate control in the illustrative embodiment are labeled as "high," "medium," or "low." Custom levels of microclimate control include a desired evaporation level and a desired temperature level (however other desired factors may also be part of a custom level).

In the illustrative embodiment, microclimate system 12 performance is measured in total heat withdrawal (W/m$^2$) and evaporative capacity (g/m$^2$-hr). In other embodiments, performance may also be measured in dry heat withdrawal (W/m$^2$). In order to ensure that the preset levels of microclimate system 12 performance are met when an automatic level is selected, the controller 60 of the exemplary microclimate system 12 considers environmental factors received from the environmental sensor unit 15 when setting operating parameters for the blower 56 and the conditioning unit 58 as shown in FIG. 5 and described herein.

For example, the high setting of the microclimate system 12 may be rated for performance of about 85 W/m$^2$ total heat withdraw and greater than 10 g/m$^2$-hr evaporative capacity. Under normal operating parameters, such performance by the microclimate system 12 may be achieved using default operating parameters in a room at about 70 degrees F. and about 50 percent humidity. However, with the blower 56 and conditioning unit 58 operating under the same normal operating parameters, performance may be degraded in a room at higher temperatures and/or humidity levels such that not enough heat withdrawal or evaporation is provided causing a patient to become wet from sweat or body fluids. Also problematic is that with the blower 56 and conditioning unit 58 operating under the normal operating parameters, performance may be undesirably increased in a room at lower temperatures and/or humidity levels such that too much heat withdrawal or evaporation is provided causing a patient to become cold. In order to maintain the rated performance in a wide range of environments, the exemplary microclimate system 12 is configured to consider environmental factors as measured by the environmental sensor unit 15 when setting operating parameters for the blower 56 and the conditioning unit 58 as further described herein.

Turning back briefly to the other buttons 54 included in the user interface 50 shown in FIG. 3, the comfort control panel 80 is configured to allow a user to set the normal firmness of the support surface 16 by adjusting the pressure in the body bladders 30. The turn-assist control panel 76 is configured to allow a user to inflate or deflate left and right turn bladders 32 in order to rotate a patient supported on the support surface about a longitudinal axis 86 of the support surface. The alarm panel 78 displays a number of alarms detected by the controller 60 and is configured to allow a user to set alarm volume or to silence a triggered alarm. The inflation control panel 80 is configured to allow a user to toggle between a normal firmness profile of the body bladders 30 and a maximum firmness profile of the body bladders 30 to facilitate patient exit from the bed 10. The weight entry panel 82 is configured to allow a user to input a patient's weight into the controller 60. The lock button 84 is configured to selectively lock out all other buttons 54 on the user interface 50 to prevent accidental operation of the user interface 50 by a user bumping the push buttons 54.

Figure 5:
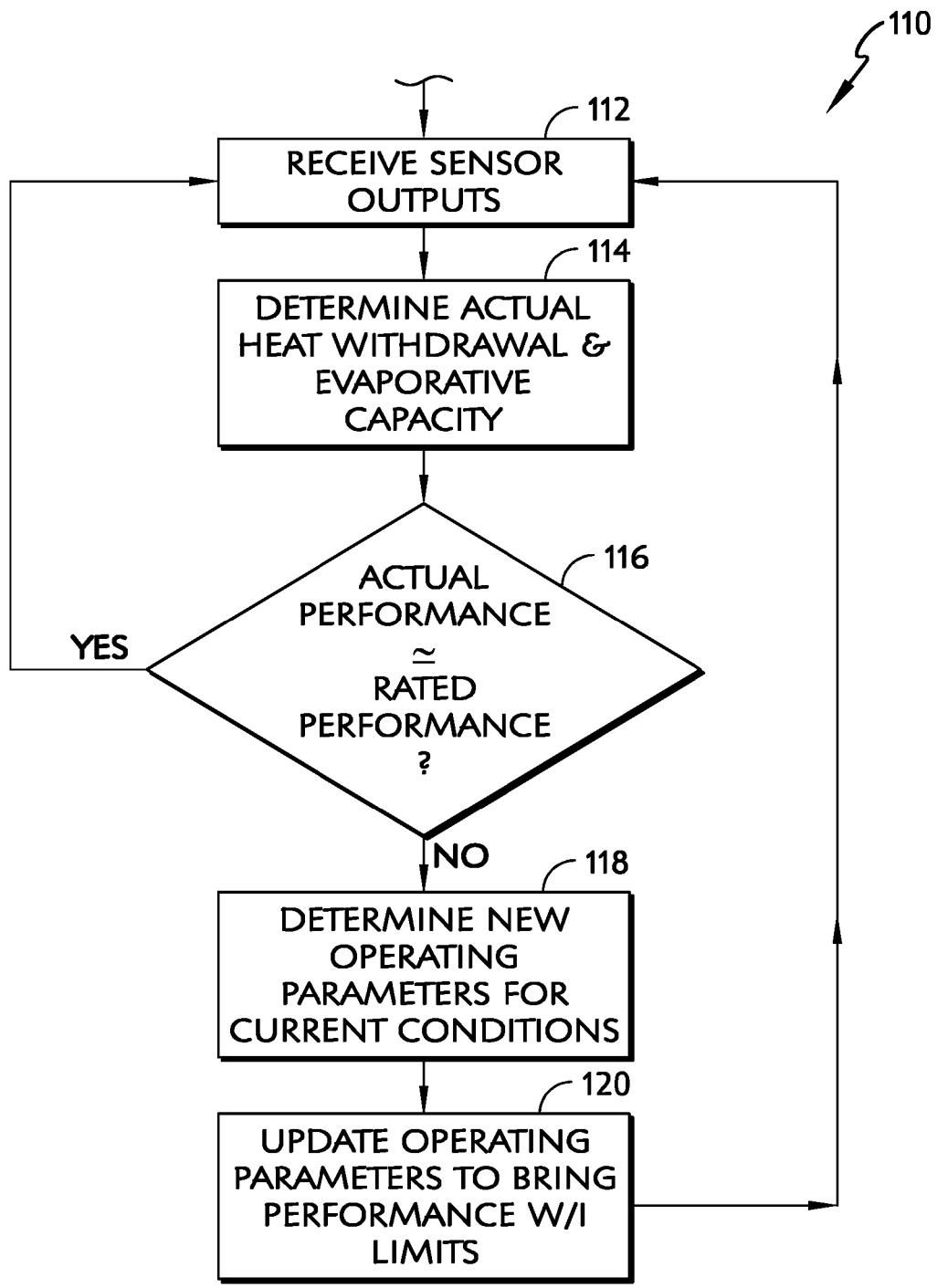
FIG. 5 is a flow chart showing a process performed by the controller of the microclimate system to account for environmental conditions during operation of the microclimate system in order to deliver rated performance in various environments.

Referring now to FIG. 5, an illustrative process 110 for controlling the microclimate system is shown. The process 110 is illustratively performed by the controller 60 of the microclimate system 12. The process 110 includes a step 112 in which the controller 60 receives sensor outputs from the environmental sensor unit 15 corresponding to environmental conditions surrounding the bed 10. The illustrative controller 60 receives a temperature input from the temperature sensor 62 a humidity input from the humidity sensor 64, and a pressure input from the pressure sensor 66 in step 112.

After receiving the sensor outputs, the process 110 advances to a step 114 in which the controller 60 determines an actual heat withdrawal and evaporative capacity performance level for the microclimate system 12. In the illustrative embodiment, the actual performance levels are determined by looking up actual performance levels from a system-specific performance look-up table. The actual heat withdrawal and evaporative capacity performance levels are looked up based on environmental factors (temperature, humidity, pressure, etc) and on current operating parameters of the air box 18 (blower speeds and conditioning unit settings corresponding to various levels of microclimate control). The system-specific performance look-up table is populated by empirical testing of a specific support surface 16 and air box 18 combination. In other embodiments, the system-specific performance look-up table may be populated by mathematical analysis of a specific support surface 16 and air box 18 combination.

In some embodiments, the controller 60 may determine the actual heat withdrawal and evaporative capacity performance level for the microclimate system 12 by plugging values corresponding to environmental factors into system-specific performance equations. The system-specific performance equations may be developed by empirical testing and/or mathematical analysis of a specific support surface 16 and air box 18 combination.

Next, the process 110 performs a decisions step 116 in which the determined actual performance levels are compared to rated performance levels for the microclimate system 12. If the actual performance levels are equal to or within an acceptable range around the rated performance levels, the process 110 loops back to step 112 and re-checks the sensor outputs. If the actual performance levels do not meet the rated performance levels, then the process 110 proceeds to a step 118.

In step 118, the process 110 determines new operating parameters for the air box 18 (blower speeds and conditioning unit settings corresponding to various levels of microclimate control) that will deliver the rated performance levels under current environmental conditions. In the illustrative embodiment, the new operating parameters are determined by looking up operating parameters from a system-specific parameter look-up table. The new operating parameters are looked up based on environmental factors (temperature, humidity, pressure). The system-specific parameter look-up table is populated by empirical testing of a specific support surface 16 and air box 18 combination. In other embodiments, the system-specific parameter look-up table may be populated by mathematical analysis of a specific support surface 16 and air box 18 combination.

In some embodiments, the controller 60 may determine the new parameters for the microclimate system 12 by plugging values corresponding to environmental factors into a set of system-specific parameter equations. The system-specific parameter equations may be developed by empirical testing and/or mathematical analysis of a specific support surface 16 and air box 18 combination.

After the new operating parameters are determined in step 118, the controller 60 proceeds to step 120 in which the current operating parameters of the air box 18 are updated to the new operating parameters determined in step 118. When the updated operating parameters are in place, the process 110 loops back to step 112 and rechecks the sensor outputs. Thus, the operating parameters of the air box 18 (blower speed and conditioning unit operation) continue to be adjusted based on environmental conditions surrounding the bed 10 detected by the environmental sensor unit 15 so that the microclimate system 12 is adapted to provide rated performance levels of heat withdrawal and evaporative capacity in almost any environment.

Figure 6:
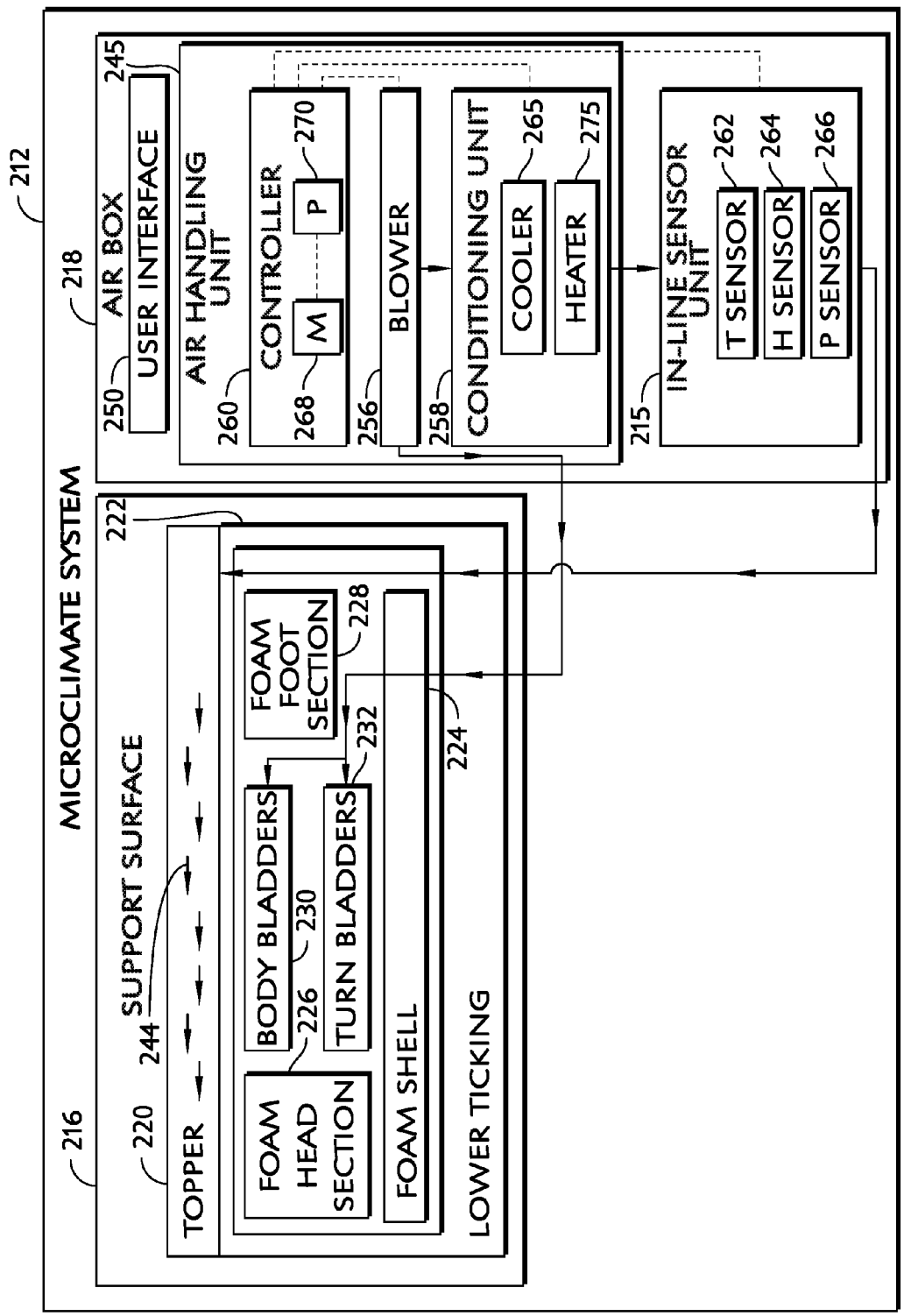
FIG. 6 is a diagrammatic view of another microclimate system including a support surface having a topper and an air box showing that the air box includes an air handling unit and an in-line sensor unit coupled between the air handling unit of the air box and the topper of the support surface.
Figure 6A:
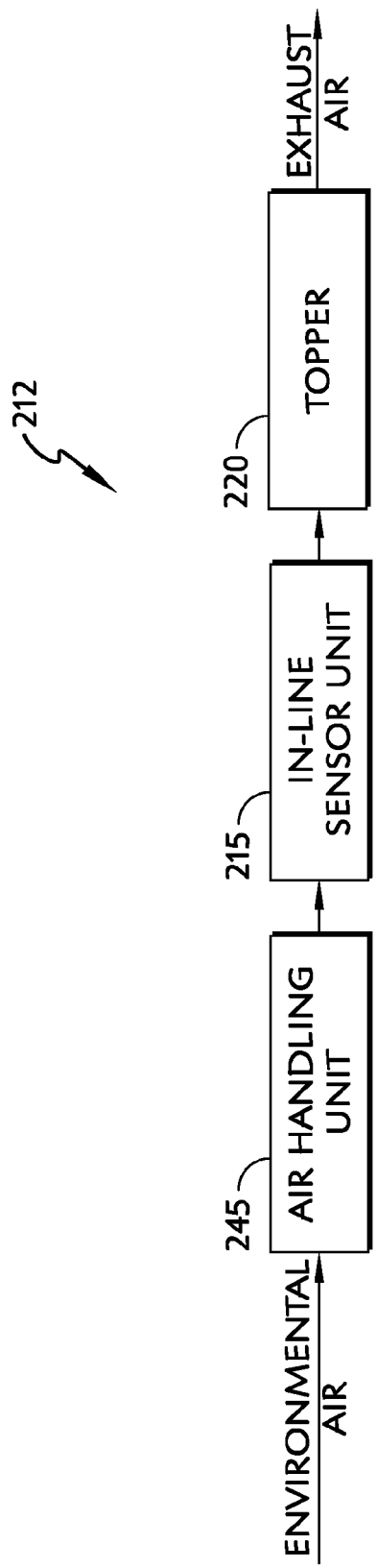
FIG. 6A is a diagrammatic pneumatic flow diagram corresponding to operation of the microclimate system of FIG. 6 showing that conditioned air is passed through the air handling unit before entering the in-line sensor unit and being sent to the topper.
Figure 7:
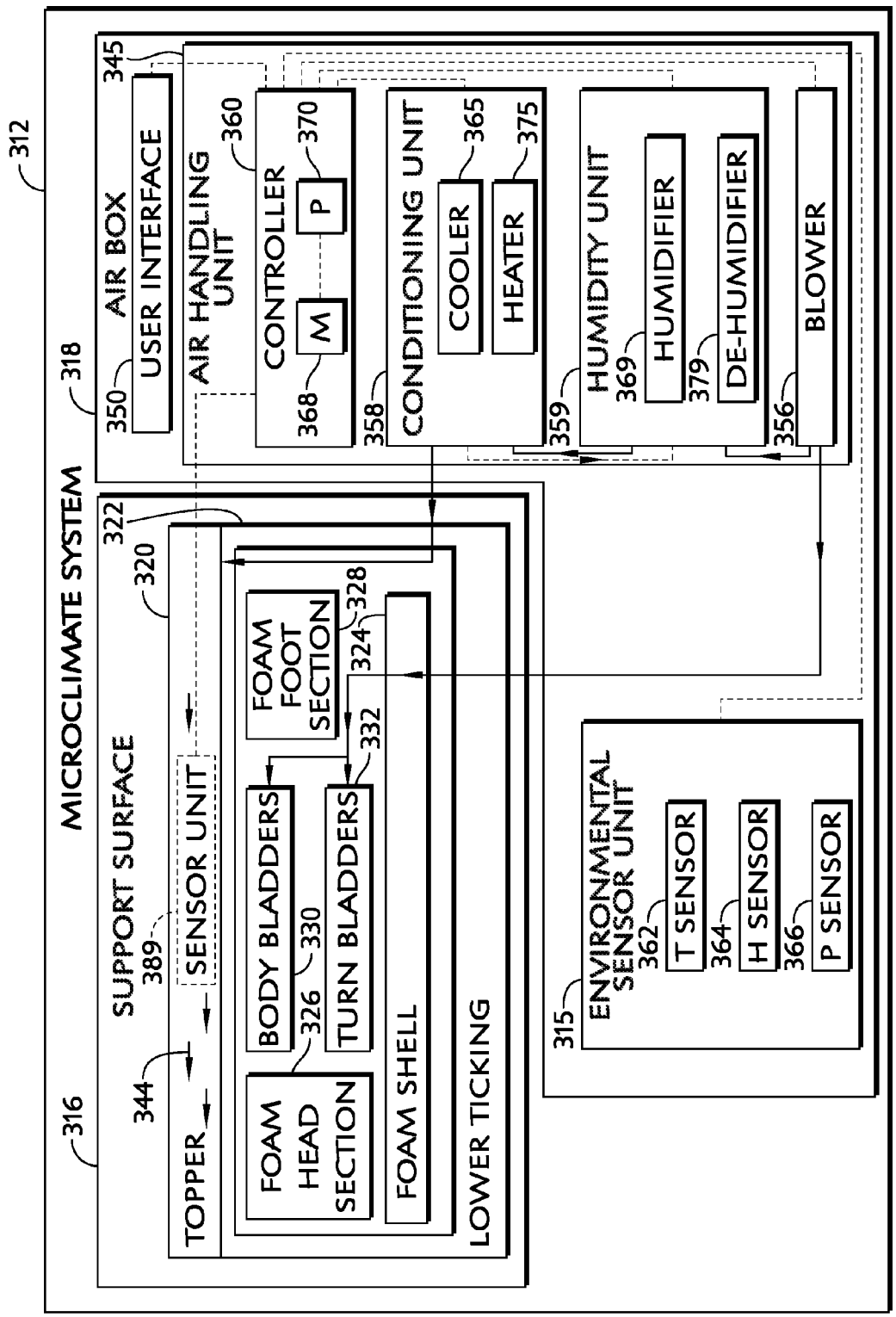
FIG. 7 is a diagrammatic view of another microclimate system including a support surface having a topper and an air box showing that the air box includes an air handling unit with a humidity unit adapted to humidify or dehumidify air passing through the air handling unit.
Figure 7A:
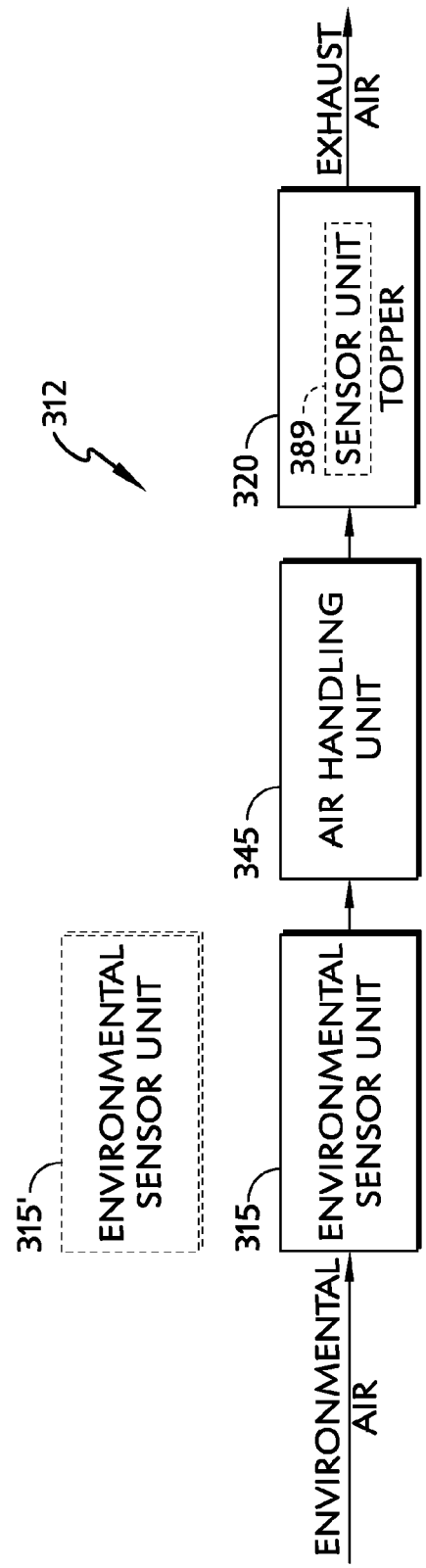
FIG. 7A is a diagrammatic pneumatic flow diagram corresponding to operation of the microclimate system of FIG. 7 showing the that environmental air is passed over the environmental sensor unit before entering the air handling unit and being sent to the topper.

Turning now to FIG. 6, another microclimate system 212 is shown diagrammatically. The microclimate system 212 is substantially similar to the microclimate system 12 shown in FIGS. 1-4 and described herein. Accordingly, similar reference numbers in the 200 series indicate features that are common between the microclimate system 12 and the microclimate system 212. The description of the microclimate system 12 is hereby incorporated by reference to apply to the microclimate system 212, except in instances when it conflicts with the specific description and drawings of the microclimate system 212. Pneumatic connections are illustrated in FIG. 6 using solid lines with arrows suggesting the direction of flow and electrical connections are illustrated in FIG. 7 with dotted lines.

Unlike the microclimate system 12 of FIGS. 1-4, the microclimate system 212 includes an in-line sensor unit 215 coupled between the air handling unit 245 and the topper 220 as shown in FIG. 6. The in-line sensor unit 215 illustratively includes a temperature sensor 262, a humidity sensor 264, and a pressure sensor 266 as shown in FIG. 6. In the illustrative embodiment, the in-line sensor unit 215 is enclosed in the housing (not shown) of the blower 218. However, in other embodiments, the in-line sensor unit 215 may be located in the connector hose (not shown) of the blower 218 or in an inlet (not shown) of the topper 220.

Each of the sensors 262, 264, 266 included in the in-line sensor unit 215 is configured to detect an input factor corresponding to the conditioned air provided to the topper 20 from the air box 18. Additionally, each of the sensors 262, 264, 266 is coupled to the controller 260 to communicate the detected input factors to the controller 260.

In operation, the microclimate system 212 is similar to the microclimate system 12 described herein. The controller 260 of the microclimate system 212 is configured to perform process 110 shown in FIG. 5 except that sensor outputs from the in-line sensor unit 215 are received and all look-ups or calculation are based on factors corresponding to the conditioned air provided to the topper 20 from the air box 18.

Turning to FIG. 7, another microclimate system 312 is shown diagrammatically. The microclimate system 312 is substantially similar to the microclimate system 12 shown in FIGS. 1-4 and described herein. Accordingly, similar reference numbers in the 300 series indicate features that are common between the microclimate system 12 and the microclimate system 312. The description of the microclimate system 12 is hereby incorporated by reference to apply to the microclimate system 312, except in instances when it conflicts with the specific description and drawings of the microclimate system 312. Pneumatic connections are illustrated in FIG. 7 using solid lines with arrows suggesting the direction of flow and electrical connections are illustrated in FIG. 7 with dotted lines.

Unlike the microclimate system 12 of FIGS. 1-4, the microclimate system 312 includes a humidity unit 359 adapted to humidify or dehumidify air supplied by the air box 318 to the topper 320 as suggested in FIG. 7. The humidity unit 359 is included in the air handling unit 345 and has a humidifier 369 and a dehumidifier 379. The humidity unit 359 is electrically coupled to the controller 360 and fluidly coupled to the blower 356 and the conditioning unit 358 so that the humidity unit 359 may be selectively operated to add or remove moisture from air pushed by the blower 356 toward the conditioning unit 358.

The humidifier 369 illustratively includes a fluid reservoir and misting element (not shown) for adding humidity to air pushed through the topper 320. The dehumidifier 379 illustratively includes a cooling chamber and cooling element (not shown) for cooling air passing through the humidity unit 359 so that water vapor condenses and falls out of the air pushed through the topper 320. In other embodiments, the dehumidifier 379 may include a desiccant-filled chamber (not shown) for absorbing humidity from air pushed through the topper 320.

In operation, the microclimate system 312 is similar to the microclimate system 12 described herein. The controller 360 of the microclimate system 312 is configured to perform process 110 shown in FIG. 5 except that operating parameters of the microclimate system 312 that may be adjusted include humidity of the air provided to the topper 320 influenced by the humidity unit 359.

In some embodiments, the humidity unit 359 may be optionally coupled to the conditioning unit 358 to receive recirculated air from the conditioning unit 358 as suggested in FIG. 7. This recirculation loop may allow the air box 318 to further adjust humidity and/or temperature of air that is eventually passed on to the topper 320.

In some embodiments, a sensor unit 389 may be optionally mounted in/on the topper 320 as shown in FIG. 7. The sensor unit 389 includes a temperature sensor and/or a humidity sensor (not shown). The sensor unit 389 is in electrical communication with the controller 36 included in the air handling unit 345 and provides feedback to the air handling unit 345 regarding the efficacy of the air handling unit 345 in maintaining conditions in the topper 320 that are not conducive to pressure ulcers (also known as bed sores).

In embodiments containing the sensor unit 389, the controller 360 monitors conditions adjacent to a patient on the topper 320. The controller 360 uses conditions from the sensor unit 389 along with environmental information from the environmental sensor unit 315 as feedback for controlling the blower 356, the conditioning unit 358, and the humidity unit 359. Thus, the controller 360 monitors and adjusts humidity, temperature, and air flow near a patient supported on the topper 320.

Based on the feedback received, the controller 360 makes decisions about whether to adjust air temperature, humidity, or air flow to the surface topper 320. The controller 360 may do nothing, or may increase/decrease humidity, or increase/decrease temperature, or increase/decrease air flow or some combination of those three. The controller 360 then uses a feedback loop to monitor state of air adjacent to the patient based on sensor unit 389 readings and then re-adjusts temperature, humidity, or amount of air flowing. In some embodiments, if needed for tighter humidity control, this controller 360 may engage the optional recirculating loop to re-adjust humidity or temperature, (prior to flowing through the topper 320). For additional control of first pass air humidity, the controller 360 may adjust cooling of the air within the humidity unit 359 or within the conditioning unit 358 to precipitate certain amount of humidity as a method of controlling humidity of cooled air. In such instances, when the air is heated back up the controller 360 calculate expected humidity.

In one example, if ambient air temp lower than needed but humidity higher than desired (depending on the state of air near a patient's skin measured by sensor unit 389 or calculated by the controller 360), the controller 360 may adjust the conditions of air provided to the topper 320. Particularly, the response of the controller 360 could be to (a) increase air flow via the blower 356 to increase mass flow of water vapor away from patient skin, and/or (b) only heat the air via the conditioning unit 358 which will result in reduced humidity, and/or c. physically reduce humidity via the humidity unit 359 (e.g. run air through desiccant, or chill air below dew point to precipitate water, then reheat), or (c) all three of (a), (b), and (c).

In another example, if ambient air temp high and humidity high (depending on the state of air near a patient's skin measured by sensor unit 389 or calculated by the controller 360), the controller 360 may adjust the conditions of air provided to the topper 320. Particularly, the controller 360 could cool air to precipitate water and reduce humidity within the humidity unit 359. The controller 360 may then reheat to adjust temperature via the conditioning unit 358. The controller 360 may or may not also include change in air flow via the blower 356.

In another example, if ambient air temperatures measured by the environmental sensor unit 315 are higher than needed and humidity is lower than needed, the controller 360 may implement a low cost and energy efficient adjustment. Particularly, the controller 360 may add water vapor to cool air. Alternatively the controller may is to only cool the air, and then monitor and adjust humidity in a selected amount to stay in a desired zone of temperature/humidity. The controller 360 may or may not change air flow via the blower 356.

In another example, if ambient air temperature is lower than needed and humidity is low, then the controller 360 may just heat air to desired temp. The controller 360 may or may not change air flow via the blower 356.

The controller 360 may increase air flow from the blower 356 when ambient air has somewhat higher humidity or in the event that the sensor unit 389 detects high temperature and/or high humidity in a zone near a patient's skin. Additionally, there may be other special cases where more air flow is provided by the controller 360 and the blower 356 such as when an incontinent event or spill is detected by the sensor unit 389 or by another sensor.

The controller 360 may decrease air flow from the blower 356 when ambient air has relatively low humidity or in the event that the sensor unit 389 detects lower temperatures and/or lower humidity in a zone near a patient's skin. Additionally, there may be other special cases where less air flow is provided by the controller 360 and the blower 356 such as when low energy consumption is warranted.

Although certain illustrative embodiments have been described in detail above, variations and modifications exist within the scope and spirit of this disclosure as described and as defined in the following claims.

The invention claimed is:

1. A microclimate system comprising
a support surface including a topper, the topper configured to conduct air along a top face of the support surface so that heat and moisture from a patient lying on the support surface are drawn away from the top face of the support surface,
an air box including a controller and a blower coupled to the controller and coupled to the topper to provide air thereto, and
an in-line sensor unit coupled to the controller, the in-line sensor unit coupled between the blower and the topper and configured to detect an input factor corresponding to air provided to the topper from the air box,
wherein the controller is configured to receive from a control panel a selected level of microclimate control including a corresponding preset level of evaporative capacity to be provided by the microclimate system along the top face of the topper, to receive indication of the input factor from the in-line sensor unit, to determine if current operating parameters of the air box provide the preset level of evaporative capacity along the top face of the topper based at least in part on the input factor, and to update the current operating parameters of the air box if the current operating parameters of the air box do not provide the preset level of evaporative capacity available along the top face of the topper.

2. The microclimate system of claim 1, wherein the in-line sensor unit includes at least one of a temperature sensor, a humidity sensor, and a pressure sensor.

3. The microclimate system of claim 2, wherein the in-line sensor unit includes a temperature sensor and a humidity sensor.

4. The microclimate system of claim 1, wherein the controller determines if current operating parameters of the air box provide the preset level of evaporative capacity along the top face of the topper based at least in part on the input factor by (i) looking up an actual level of evaporative capacity corresponding to the detected input factor in a first look-up table and (ii) comparing the actual level of evaporative capacity with the preset level of evaporative capacity available along the top face of the topper.

5. The microclimate system of claim 4, wherein the controller updates the current operating parameters of the air box by (i) looking up new operating parameters corresponding to the detected input factor in a second look-up table and (ii) changing the current operating parameters to the new operating parameters.

6. The microclimate system of claim 1, wherein the air box includes a conditioning unit coupled to the controller, and the conditioning unit is coupled between the blower and the topper.

7. The microclimate system of claim 6, wherein the conditioning unit includes at least one of a heater configured to warm air moving from the blower to the topper and a cooler configured to cool air moving from the blower to the topper.

8. The microclimate system of claim 7, wherein the operating parameters of the air box include blower speed settings and conditioning unit power settings.

9. The microclimate system of claim 1, wherein the selected level of microclimate control includes a corresponding preset level of heat withdrawal to be provided by the microclimate system along the top face of the topper and the controller is configured to determine if current operating parameters of the air box provide the preset level of heat withdrawal based at least in part on the input factor and to update the current operating parameters of the air box if the current operating parameters of the air box do not provide both the preset level of evaporative capacity and the preset level of heat withdrawal.

10. The microclimate system of claim 9, wherein the air box includes a conditioning unit coupled to the controller, the conditioning unit includes at least one of a heater configured to warm air moving from the blower to the topper and a cooler configured to cool air moving from the blower to the topper, and the operating parameters to be updated if the current operating parameters of the air box do not provide the preset level of evaporative capacity or the preset level of heat withdrawal include blower speed settings that adjust the volume of air from the air box and conditioning unit power settings that adjust the temperature of air from the air box.

11. The microclimate system of claim 1, wherein the air box includes a housing and a connector hose that extends between the housing and the topper, and the in-line sensor unit is disposed in the connector hose.

12. A microclimate system comprising
a topper,
an air box including a controller and a blower coupled to the controller and coupled to the topper to provide air thereto, and
an in-line sensor unit coupled the controller and configured to detect an input factor corresponding to air provided from the blower to the topper,
wherein the controller is configured to receive a preset level of evaporative capacity to be provided by the microclimate system along the top face of the topper, to receive indication of the input factor from the environmental sensor unit, to determine if current operating parameters of the air box provide the preset level of evaporative capacity based at least in part on the input factor, and to update the current operating parameters of the air box if the current operating parameters of the air box do not provide the preset level of evaporative capacity.

13. The microclimate system of claim 12, wherein the air box includes a housing and a connector hose that extends between the housing and the topper, and the in-line sensor unit is disposed in the connector hose.

14. The microclimate system of claim 12, wherein the air box includes a conditioning unit coupled to the controller, the conditioning unit coupled between the blower and the topper, and the conditioning unit including at least one of a heater configured to warm air moving from the blower to the topper and a cooler configured to cool air moving from the blower to the topper.

15. The microclimate system of claim 14, wherein the operating parameters of the air box include blower speed settings and conditioning unit power settings.

16. The microclimate system of claim 12, wherein the in-line sensor unit is coupled between the blower and the topper.

17. A method for controlling a microclimate system including a topper and an air box coupled to the topper to provide pressurized air to the topper, the method comprising
receiving from a control panel a preset level of evaporative capacity to be provided by the microclimate system along a top face of the topper,
receiving information that corresponds to air provided to the topper from the air box from a sensor unit that is coupled between a blower of the air box and the topper,
determining if current operating parameters of the air box provide the preset level of evaporative capacity through the topper based at least in part on the information, and
updating the current operating parameters of the air box if the current operating parameters of the air box do not provide the preset level of evaporative capacity through the topper.

18. The method of claim 17, wherein determining if current operating parameters of the air box provide the preset level of evaporative capacity includes (i) looking up an actual level of evaporative capacity corresponding to the received information in a first look-up table and (ii) comparing the actual level of evaporative capacity parameters with the preset level of evaporative capacity.

19. The method of claim 18, wherein updating the current operating parameters of the air box includes (i) looking up new operating parameters corresponding to the received information in a second look-up table and (ii) changing the current operating parameters to the new operating parameters.

20. The method of claim 17, wherein the information received corresponds to at least one of temperature, humidity, and pressure of air provided to the topper from the air box.

21. The method of claim 17, wherein determining if current operating parameters of the air box provide the evaporative capacity includes (i) calculating an actual level of evaporative capacity corresponding to the received information using a first equation and (ii) comparing the actual level of evaporative capacity with the preset level of evaporative capacity.

* * * * *